(12) United States Patent
Morishima et al.

(10) Patent No.: US 10,266,871 B2
(45) Date of Patent: Apr. 23, 2019

(54) MEASUREMENT METHOD FOR THROMBIN PRODUCTION

(71) Applicant: DAIICHI SANKYO COMPANY, LIMITED, Tokyo (JP)

(72) Inventors: Yoshiyuki Morishima, Tokyo (JP); Yuko Honda, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 12 days.

(21) Appl. No.: 14/653,824

(22) PCT Filed: Dec. 17, 2013

(86) PCT No.: PCT/JP2013/083688
§ 371 (c)(1),
(2) Date: Jun. 18, 2015

(87) PCT Pub. No.: WO2014/098056
PCT Pub. Date: Jun. 26, 2014

(65) Prior Publication Data
US 2015/0322480 A1 Nov. 12, 2015

(30) Foreign Application Priority Data

Dec. 18, 2012 (JP) ................................. 2012-275671

(51) Int. Cl.
*C12Q 1/56* (2006.01)
*G01N 33/86* (2006.01)

(52) U.S. Cl.
CPC .............. *C12Q 1/56* (2013.01); *G01N 33/86* (2013.01); *G01N 2333/974* (2013.01)

(58) Field of Classification Search
CPC ........ A61K 31/57; A61K 31/47; A61K 31/16; A61K 31/4375; A61K 31/496; A61K 31/573; A61K 31/58; A61K 31/66; A61K 31/77; A61K 31/535; A61K 31/4709; A61K 31/5383; A61K 2300/00; A61K 45/06; A61K 9/0043; A61K 9/0046; A61K 9/0048; G01N 33/86; G01N 2333/726; G01N 2333/75; G01N 2333/96447; G01N 2333/974; G01N 2333/745; G01N 2333/8128; G01N 2800/52; G01N 33/557; C12Q 1/56; C12Q 2337/12; A61L 15/60; C08F 6/006; C08J 2300/14; C08J 3/28; Y10S 514/912; Y10S 514/913; Y10T 428/2982
See application file for complete search history.

(56) References Cited

U.S. PATENT DOCUMENTS

| 5,192,689 | A | 3/1993 | Hemker |
| 5,563,041 | A | 10/1996 | Reers |
| 2005/0221414 | A1 | 10/2005 | Varadi |
| 2007/0254325 | A1 | 11/2007 | Rechner |
| 2008/0261254 | A1 | 10/2008 | Weyl |
| 2009/0280570 | A1 | 11/2009 | Kawasaki |
| 2010/0009396 | A1 | 1/2010 | Hilbert |
| 2013/0302839 | A1* | 11/2013 | Harenberg ............... C12Q 1/56 435/13 |

FOREIGN PATENT DOCUMENTS

| JP | 2811799 | 10/1998 |
| JP | 3137261 | 2/2001 |
| JP | 3684451 | 8/2005 |
| JP | 3792198 | 7/2006 |
| JP | 2006-329643 | 12/2006 |
| JP | 2007-530963 | 11/2007 |
| JP | 2008-281560 | 11/2008 |
| JP | 2010-515045 | 5/2010 |
| JP | 4989292 | 8/2012 |
| WO | 2000/049402 | 8/2000 |
| WO | 2001/096879 | 12/2001 |
| WO | 2003/093831 | 11/2003 |
| WO | 2006/117246 | 11/2006 |

OTHER PUBLICATIONS

Cattaneo, MArco "New P2Y12 Inhibitors" Circulation, 2010, 121, pp. 171-179. doi.org/10.1161/CIRCULATIONAHA.109.853069.*
Extended European Search Report for European Application No. 13865021.3, dated May 30, 2016.
Wong P.C. et al., "Razaxaban, a direct factor Xa inhibitor, in combination with aspirin and/or clopidogrel improves low-dose antithrombotic activity without enhancing bleeding liability in rabbits,"J. Thromb. Thrombolysis; vol. 24, No. 1, pp. 43-51 (Feb. 24, 2007)

(Continued)

*Primary Examiner* — Aaron J Kosar
(74) *Attorney, Agent, or Firm* — Locke Lord LLP

(57) ABSTRACT

It is an object of the present invention to provide a measurement method capable of easily evaluating combined effects in a single assay system, when antithrombotic agents having different mechanisms of action are used in combination. A method for measuring thrombin generation comprising: (1) a step of adding an anticoagulant, a $P2Y_{12}$ receptor inhibitor, adenosine diphosphate and tissue factor to platelet rich plasma; (2) a step of adding a fluorogenic thrombin substrate and a calcium-containing solution thereto; and (3) a step of measuring fluorescence intensity.

23 Claims, 10 Drawing Sheets

(56) References Cited

OTHER PUBLICATIONS

Andre P. et al., "Anticoagulants (thrombin inhibitors) and aspirin synergize with P2Y12 recepter antagonism in thrombosis," Circulation, vol. 108, No. 21, pp. 2697-2703 (Nov. 25, 2003).
Wegert, W., et al., "Effects of antiplatelet agents on platelet-induced thrombin generation" International Journal of Clinical Pharmacology and Therapeutics, 40(4):135-141 (2002).
Altman, R., et al., "Thrombin generation by activated factor VII on platelet activated by different agonists. Extending the cell-based model of hemostasis"; Thrombosis Journal, 4:5 (2006).
Savi, P., et al. "Identification and biological activity of the active metabolite of clopidogrel"; Thromb Haemost; 84:891-6 (2000).
International Search Report (English translation) issued in corresponding International PCT Application No. PCT/JP2013/083688, dated Feb. 18, 2014.
Written Opinion (English translation) issued in corresponding International PCT Application No. PCT/JP2013/083688, dated Feb. 18, 2014.

* cited by examiner

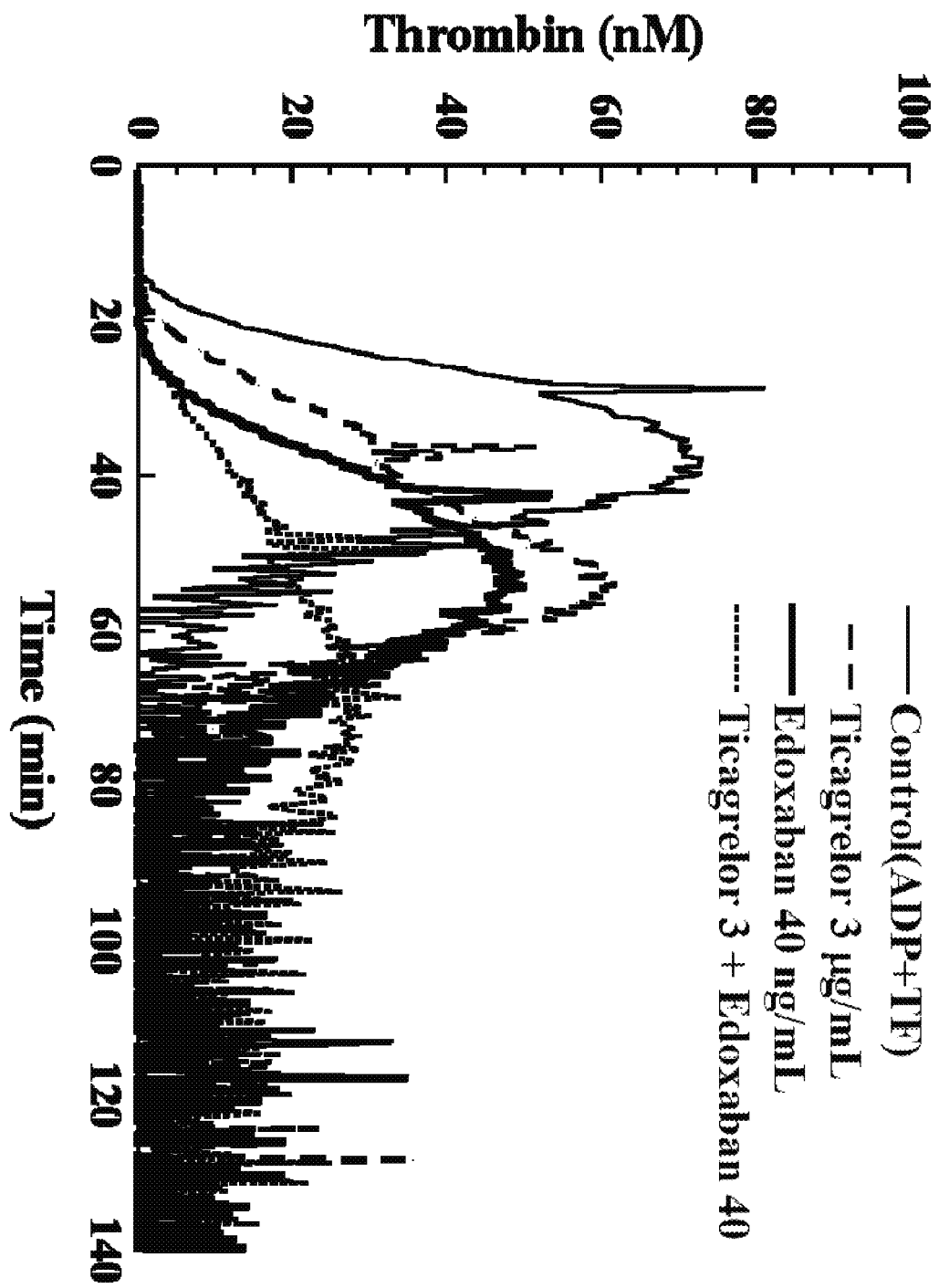

MEASUREMENT METHOD FOR THROMBIN PRODUCTION

This application is a national phase entry under 35 U.S.C. § 371 of International Application Number PCT/JP2013/083688, filed Dec. 17, 2013, entitled "MEASUREMENT METHOD FOR THROMBIN PRODUCTION", which claims the benefit of Japanese Patent Application Number JP 2012-275671, filed Dec. 18, 2012, all of which are hereby incorporated by reference in their entireties.

BACKGROUND OF THE INVENTION

Field of the Invention

The present invention relates to a method for measuring thrombin generation.

Description of the Related Art

As an indicator for evaluating thrombosis and hemostasis ability in vivo, a method for measuring thrombin generation in plasma has been known (for example, Patent Literatures 1, 2, 3, etc.). Moreover, a measurement method for evaluating the effect of an antiplatelet agent on thrombin generation has also been known (for example, Non Patent Literature 1, etc.). Furthermore, a measurement method for evaluating the effect of a combination of a platelet agonist and a factor VIIa on thrombin generation has also been known (for example, Non Patent Literature 2, etc.).

CITATION LIST

Patent Literature

Patent Literature 1: WO 03/093831
Patent Literature 2: WO 2006/117246
Patent Literature 3: U.S. Pat. No. 5,192,689

Non Patent Literature

Non Patent Literature 1: International Journal of Clinical Pharmacology and Therapeutics, Vol. 40-No. 4/2002 (135-141)
Non Patent Literature 2: Thrombosis Journal 2006, 4:5

BRIEF SUMMARY OF THE INVENTION

Technical Problem

At present, as antithrombotic agents, antiplatelet agents, anticoagulants and the like have been used. Antiplatelet agents and anticoagulants suppress the formation of thrombus based on different mechanisms. The pharmacological activity of an antiplatelet agent can be revealed, for example, by measuring the inhibitory activity of the agent on platelet aggregation, whereas the pharmacological activity of an anticoagulant can be revealed, for example, by measuring the prolongation activity of the agent on blood clotting time. However, basically, the antiplatelet agent does not influence blood clotting time, and the anticoagulant does not influence platelet aggregation.

Thus, even if a measurement method for blood clotting time or platelet aggregation has been applied to the combined use of these agents, the combined effects could not be evaluated.

Accordingly, it is an object of the present invention to provide a measurement method capable of easily evaluating combined effects in a single assay system, when antithrombotic agents having different mechanisms of action are used in combination.

Solution to Problem

The present invention provides the following:
(1) A method for measuring thrombin generation comprising: (a) a step of adding an anticoagulant, a $P2Y_{12}$ receptor inhibitor, adenosine diphosphate (hereinafter also referred to as "ADP") and tissue factor (hereinafter also referred to as "TF") to platelet rich plasma (hereinafter also referred to as "PRP"); (b) a step of adding a fluorogenic thrombin substrate and a calcium-containing solution thereto; and (c) a step of measuring fluorescence intensity;
(2) The method according to (1) above, wherein the anticoagulant is a factor Xa inhibitor;
(3) The method according to (2) above, wherein the factor Xa inhibitor is Edoxaban;
(4) The method according to any one of (1) to (3) above, wherein the $P2Y_{12}$ receptor inhibitor is Clopidogrel or Ticagrelor;
(5) The method according to any one of (1) to (4) above, wherein the final concentration of ADP in step (a) is 5 to 20 µM;
(6) The method according to any one of (1) to (5) above, wherein the final concentration of TF in step (a) is 0.05 to 0.25 pM;
(7) The method according to any one of (1) to (6) above, further comprising a step of converting the fluorescence intensity obtained in step (c) to a thrombin concentration;
(8) A method for measuring thrombin generation comprising: (d) a step of obtaining PRP from blood collected from a mammal to which an anticoagulant and a $P2Y_{12}$ receptor inhibitor have been administered; (e) a step of adding ADP and TF to the obtained PRP; (f) a step of further adding a calcium-containing solution and a fluorogenic thrombin substrate thereto; and (g) a step of measuring fluorescence intensity;
(9) The method according to (viii) above, further comprising a step of converting the fluorescence intensity obtained in step (g) to a thrombin concentration;
(10) A method for evaluating the combined effects of an anticoagulant and a $P2Y_{12}$ receptor inhibitor, comprising: (h) a step of obtaining PRP from blood collected from a mammal to which an anticoagulant and a $P2Y_{12}$ receptor inhibitor have been administered; (i) a step of adding ADP and TF to the obtained PRP; (j) a step of further adding a calcium-containing solution and a fluorogenic thrombin substrate thereto; (k) a step of measuring fluorescence intensity; (l) a step of obtaining PRP from blood collected from a mammal to which an anticoagulant or a $P2Y_{12}$ receptor inhibitor have been administered, or to which none of the agents have been administered; (m) a step of adding ADP and TF to the obtained PRP; (n) a step of further adding a calcium-containing solution and a fluorogenic thrombin substrate thereto; (o) a step of measuring fluorescence intensity; and (p) a step of comparing the value obtained in step (k) with the value obtained in step (o);
(11) A method for evaluating the combined effects of an anticoagulant and a $P2Y_{12}$ receptor inhibitor, comprising: (q) a step of obtaining PRP from blood collected from a mammal to which an anticoagulant and a $P2Y_{12}$ receptor inhibitor have been administered; (r) a step of adding ADP and TF to the obtained PRP; (s) a step of further adding a calcium-containing solution and a fluorogenic thrombin substrate thereto; (t) a step of measuring fluorescence intensity; (u) a step of converting the fluorescence intensity obtained in step (t) to a thrombin concentration; (v) a step of obtaining PRP from blood collected from a mammal to which an anticoagulant or a $P2Y_{12}$ receptor inhibitor have been administered, or to which none of the agents have been administered; (w) a step of adding ADP and TF to the obtained PRP; (x) a step of further adding a calcium-containing solution and a fluorogenic thrombin substrate thereto; (y) a step of measuring fluorescence intensity; (z) a step of converting the fluorescence intensity obtained in step (y) to a thrombin concentration; and (aa) a step of comparing the value obtained in step (u) with the value obtained in step (z); and

(12) A method for measuring thrombin generation comprising: (q) a step of adding adenosine diphosphate and tissue factor to platelet rich plasma that contains an anticoagulant and a $P2Y_{12}$ receptor inhibitor; (r) a step of adding a fluorogenic thrombin substrate and a calcium-containing solution thereto; and (s) a step of measuring fluorescence intensity.

Advantageous Effects of the Invention

The present invention has the effect of easily measuring the combined effects of antithrombotic agents. In addition, the present invention also has the effect of predicting a bleeding risk caused by administration of an anticoagulant and/or a $P2Y_{12}$ receptor inhibitor, using thrombin generation as an indicator.

BRIEF DESCRIPTION OF THE SEVERAL VIEWS OF THE DRAWINGS

FIG. 5A shows the effects of control, Ticagrelor (3 μg/mL), Edoxaban (40 ng/mL), and Ticagrelor (3 μg/mL)+Edoxaban (40 ng/mL) on thrombin generation. The longitudinal axis indicates a thrombin concentration (nM), and the horizontal axis indicates a time (min).

DETAILED DESCRIPTION OF THE INVENTION

Figure 1:
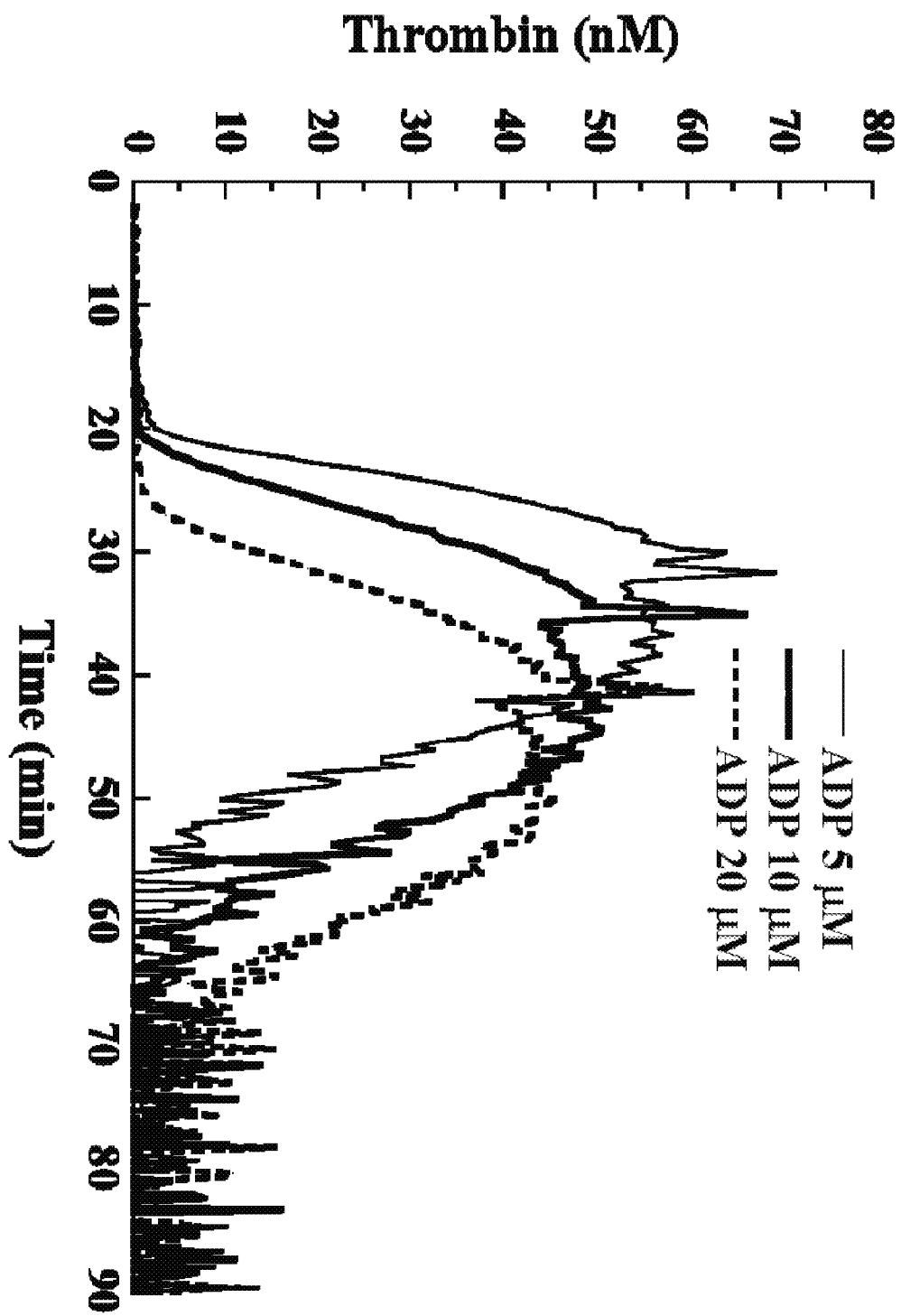
FIG. 1 shows the effect of ADP alone (concentration: 5 to 20 μM) on thrombin generation. The longitudinal axis indicates a thrombin concentration (nM), and the horizontal axis indicates a time (min).

The present invention relates to a method for measuring thrombin generation comprising a step of adding an anticoagulant, a $P2Y_{12}$ receptor inhibitor, ADP and TF to PRP, a step of further adding a calcium-containing solution and a fluorogenic thrombin substrate to the PRP, and a step of measuring fluorescence.

The PRP used in the present invention is not particularly limited, as long as it is the PRP of a mammal. It is preferably human PRP. Such PRP can be obtained by collecting blood from a mammal using a syringe filled with, for example, sodium citrate, EDTA or the like, and preferably with sodium citrate, and then subjecting the obtained blood to centrifugation to collect a supernatant.

The anticoagulant used in the present invention is not particularly limited. Examples of the anticoagulant include Dabigatran, Argatroban, Hirudin, Heparin, Enoxaparin, Dalteparin, Warfarin, Fondaparinux, Edoxaban, Rivaroxaban, Apixaban, Betrixaban, Otamixaban, salts thereof, and active metabolites thereof.

The $P2Y_{12}$ receptor inhibitor used in the present invention is an agent that binds to the $P2Y_{12}$ class of an ADP receptor on a platelet and inhibits platelet activation and/or aggregation. The $P2Y_{12}$ receptor inhibitor is not particularly limited. Examples of the $P2Y_{12}$ receptor inhibitor include Ticlopidine, Clopidogrel, Prasugrel, Elinogrel, Ticagrelor, Cangrelor, salts thereof, and active metabolites thereof.

In the present description, the "salt" means a salt formed by allowing a free base of an anticoagulant or a $P2Y_{12}$ receptor inhibitor to react with an acid or a base. In the present description, the "active metabolite" means a compound exhibiting anticoagulant action or antiplatelet action, which is formed as a result of the chemical structure of an anticoagulant or a $P2Y_{12}$ receptor inhibitor administered to a living body having been changed by enzymatic or chemical metabolism in the living body.

The final concentration of the ADP used in the present invention is preferably 5 to 20 μM, and more preferably 10 μM.

The TF used in the present invention may be either a recombinant tissue factor or a non-recombinant tissue factor. It is preferably a recombinant tissue factor, and more preferably a recombinant human tissue factor. Such TF can be purchased from, for example, Thrombinoscope BV, Dade Behring, etc. The final concentration of TF used in step 1 is preferably 0.05 to 1 pM, more preferably 0.05 to 0.25 pM, and further preferably 0.25 pM.

In the present invention, the order of adding an anticoagulant, a $P2Y_{12}$ receptor inhibitor, ADP and TF to PRP is not particularly limited. It is preferably the order of adding an anticoagulant and a $P2Y_{12}$ receptor inhibitor, and then adding ADP and TF.

The calcium-containing solution used in the present invention is preferably a calcium chloride-containing solution. The fluorogenic thrombin substrate used in the present invention is not particularly limited, as long as it is degraded by thrombin and emits fluorescence. An example of such a fluorogenic thrombin substrate is Z-Gly-Gly-Arg-AMC●HCl sold by Bachem. As a fluorogenic probe, 7-amido-4-methyl-coumalin (AMC) or the like is used. AMC is excited at 390 nm and is released at 460 nm.

As described above, the calcium-containing solution and the fluorogenic thrombin substrate can be acquired, separately. Otherwise, FluCa-kit (manufactured by Thrombinoscope BV) comprising both of the above components may also be used.

In the present invention, in order to measure the concentration of the generated thrombin, fluorescence intensity is measured. The reason that fluorescence intensity is measured instead of directly measuring the concentration of thrombin is as follows. The fluorogenic thrombin substrate leaves a fluorogenic probe as a result of degradation by thrombin. Since the fluorescence intensity of the thus released fluorogenic probe depends on the concentration of thrombin, the thrombin concentration can be indirectly determined by measuring fluorescence intensity.

In order to convert the fluorescence intensity to a thrombin concentration, it is preferable that a calibration curve be previously prepared. Alternatively, using Thrombin Calibrator, FluCa-kit and Thrombinoscope software, which are available from Thrombinoscope BV, the fluorescence intensity can be easily converted to a thrombin concentration.

The method of measuring fluorescence intensity is, for example, a method of measuring fluorescence intensity using a fluorophotometer (Fluoskan Ascent, manufactured by Themo Scientific). Moreover, in order to convert the fluorescence intensity that has been measured over time to a thrombin concentration, Thrombinoscope software manufactured by Thrombinoscope BV is preferably used.

Parameters used to evaluate thrombin generation include "Lag time (min)" indicating a time that elapses before initiation of thrombin generation, "Time to Peak (min)" indicating a time at which the thrombin concentration reaches the maximum, "ETP (nM×min)" indicating the area under the thrombin concentration curve, "Peak (nM)" indicating the maximum value of the thrombin concentration, and "MaxR (nM/min)" indicating the maximum velocity of thrombin generation. MaxR can be calculated according to the following formula.

$$\mathrm{Max}R = \frac{\mathrm{Peak}}{\mathrm{Time\ to\ peak} - \mathrm{Lag\ time}} \quad \text{[Expression 1]}$$

Thrombin is an enzyme that converts fibrinogen to soluble fibrin and activates factor XIII. Soluble fibrin is converted to insoluble fibrin by factor XIIIa. Accordingly, if the generation of thrombin can be suppressed, the production of insoluble fibrin can also be suppressed. Therefore, according to the present invention, the antithrombotic effect obtained when an anticoagulant and a $P2Y_{12}$ receptor inhibitor are used in combination can be determined in a single assay system.

In order to determine the antithrombotic effect obtained when an anticoagulant and a $P2Y_{12}$ receptor inhibitor are used in combination, the above described method for measuring thrombin generation may be applied. For example, the antithrombotic effect can be evaluated by performing the following steps:

(h) a step of obtaining platelet rich plasma from blood collected from a mammal to which an anticoagulant and a $P2Y_{12}$ receptor inhibitor have been administered;
(i) a step of adding adenosine diphosphate and tissue factor to the obtained platelet rich plasma;
(j) a step of further adding a calcium-containing solution and a fluorogenic thrombin substrate thereto;
(k) a step of measuring fluorescence intensity;
(l) a step of obtaining platelet rich plasma from blood collected from a mammal to which an anticoagulant or a $P2Y_{12}$ receptor inhibitor have been administered, or to which none of the agents have been administered;
(m) a step of adding adenosine diphosphate and tissue factor to the obtained platelet rich plasma;
(n) a step of further adding a calcium-containing solution and a fluorogenic thrombin substrate thereto;
(o) a step of measuring fluorescence intensity; and
(p) a step of comparing the value obtained in step (k) with the value obtained in step (o).

When the value obtained in step (k) is compared with the value obtained in step (o), the fluorescence intensity is converted to a thrombin concentration using Thrombinoscope software or the like, and thereafter, a comparison is made in terms of each of Lag time (min), Time to Peak (min), ETP (nM×min), Peak (nM), and MaxR (nM/min). If there is a significant difference in at least one parameter, it can be determined that there are combined effects. Whether the combined effects are additive effects or synergic effects is determined from various viewpoints.

Since both the anticoagulant and the $P2Y_{12}$ receptor inhibitor are agents for suppressing thrombus formation, bleeding may occur after administration of these agents. The present invention can also be utilized to predict such a bleeding risk using Lag time (min), Time to Peak (min), ETP (nM×min), Peak (nM), and/or MaxR (nM/min).

The present invention also provides a kit for measuring thrombin generation, which comprises adenosine diphosphate, tissue factor, a fluorogenic thrombin substrate, and a calcium-containing solution.

Hereinafter, the present invention will be described in detail in the following examples. However, these examples are not intended to limit the scope of the present invention.

EXAMPLES

Preparation of HEPES Buffer

HEPES and sodium chloride were dissolved in distilled water, so that the two reagents had concentrations of 20 mM and 140 mM, respectively, and thereafter, using a 1 mol/L sodium hydroxide solution, the pH of the solution was adjusted to pH 7.4. The thus obtained solution was preserved at 4° C. Upon use, bovine serum albumin (BSA) (final concentration: 0.5%) was added to the solution.

Preparation of ADP Solution

ADP was dissolved in a BSA-added HEPES buffer to a concentration of 10 mM, and the obtained solution was then preserved at −30° C. Upon use, it was unfrozen, and it was then diluted with a BSA-added HEPES buffer to a suitable concentration.

Preparation of TF Solution 1 vial of PRP reagent (manufactured by Thrombinoscope BV) was dissolved in 1 mL of distilled water (TF concentration: 6 pM). The obtained solution was diluted with a HEPES buffer to which BSA had not been added, and was then used.

Preparation of Edoxaban Solution

Edoxaban tosilate hydrate was dissolved in dimethyl sulfoxide (DMSO), and the obtained solution was then diluted with saline to a DMSO concentration of 1%.

Preparation of Clopidogrel Solution

An active metabolite of Clopidogrel (2-{1-[(1S)-1-(2-chlorophenyl)-2-methoxy-2-oxoethyl]-4-sulfanyl-3-piperidinyli-diene}acetic acid, Thromb Haemost 2000; 84:891-6) was dissolved in methanol, and the obtained solution was then diluted with saline to a methanol concentration of 5%.

Preparation of Ticagrelor Solution

Ticagrelor was dissolved in DMSO.

Preparation of Human PRP

Using a syringe filled with 2 mL of a solution containing 38 mg/mL sodium citrate, 18 mL of blood was collected from the radial vein of a healthy volunteer. The obtained blood was centrifuged at room temperature at 150×g for 10 minutes, so that a supernatant was obtained as PRP. The residue obtained after separation of the PRP was centrifuged at room temperature at 2000×g for 10 minutes, so that a supernatant was obtained as platelet poor plasma (hereinafter also referred to as "PPP"). The PRP was diluted with the PPP, so that the number of platelets in the PRP could be $2×10^5$ platelets/μL. The obtained PRP was left at 16° C. for 30 minutes or more, and it was then used for the measurement of thrombin generation.

Studies Regarding Measurement Conditions

10 μL of a 1% DMSO-containing saline was added to a 96-well plate, and 70 μL of the above obtained human PRP was then added thereto. Thereafter, 20 μL of an ADP solution (final concentration: 5, 10 or 20 μM), or 20 μL of a solution prepared by mixing an ADP solution (final concentration: 10 μM) and a TF solution (final concentration: 0.05 or 0.25 pM) in equal volumes, was added to the plate, and the obtained mixture was then incubated at 37° C.

To a well used for the calibration curve of thrombin concentration, 20 μL of Thrombin Calibrator (manufactured by Thrombinoscope BV) was added, instead of adding an ADP solution or a TF solution.

Five to seven minutes later, 20 μL of the heated FluCa-kit liquid (manufactured by Thrombinoscope BV) was added to the well, so that the reaction was initiated. Using a fluorophotometer (Fluoroskan Ascent, manufactured by Thermo Scientific), the fluorescence intensity at ex 390 nm/em 460 nm was measured at 37° C. for 150 minutes, and using Thrombinoscope software (manufactured by Thrombinoscope BV), Lag time (min), Time to Peak (min), ETP (nM×min), Peak (nM), and MaxR (nM/min) were calculated. The measurement was carried out in triplicate measurements.

The time course of the thrombin concentration is shown in FIG. 1. It was found that ADP provokes thrombin generation. In addition, it was also found that the ADP concentration has an influence on Peak, Lag time, and Time to Peak.

Figure 2:
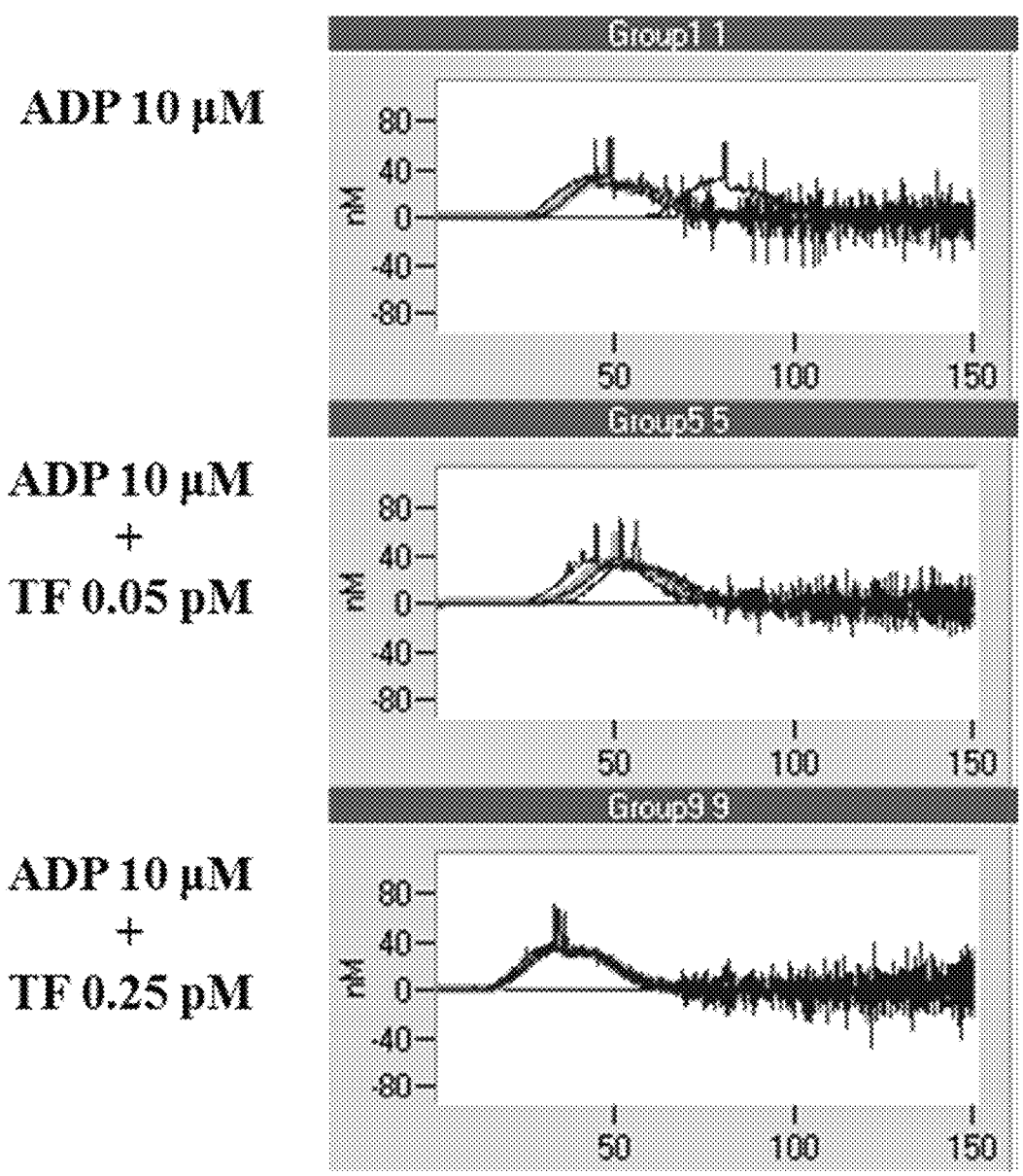
FIG. 2 shows the influence of ADP and TF on thrombin generation (triplicate measurements). The upper graph shows the effect of ADP (10 μM) on thrombin generation. The middle graph shows the effect of ADP (10 μM) and TF (0.05 pM) on thrombin generation. The lower graph shows the effect of ADP (10 μM) and TF (0.25 pM) on thrombin generation. The longitudinal axis indicates a thrombin concentration (nM), and the horizontal axis indicates a time (min).
Figure 3A:
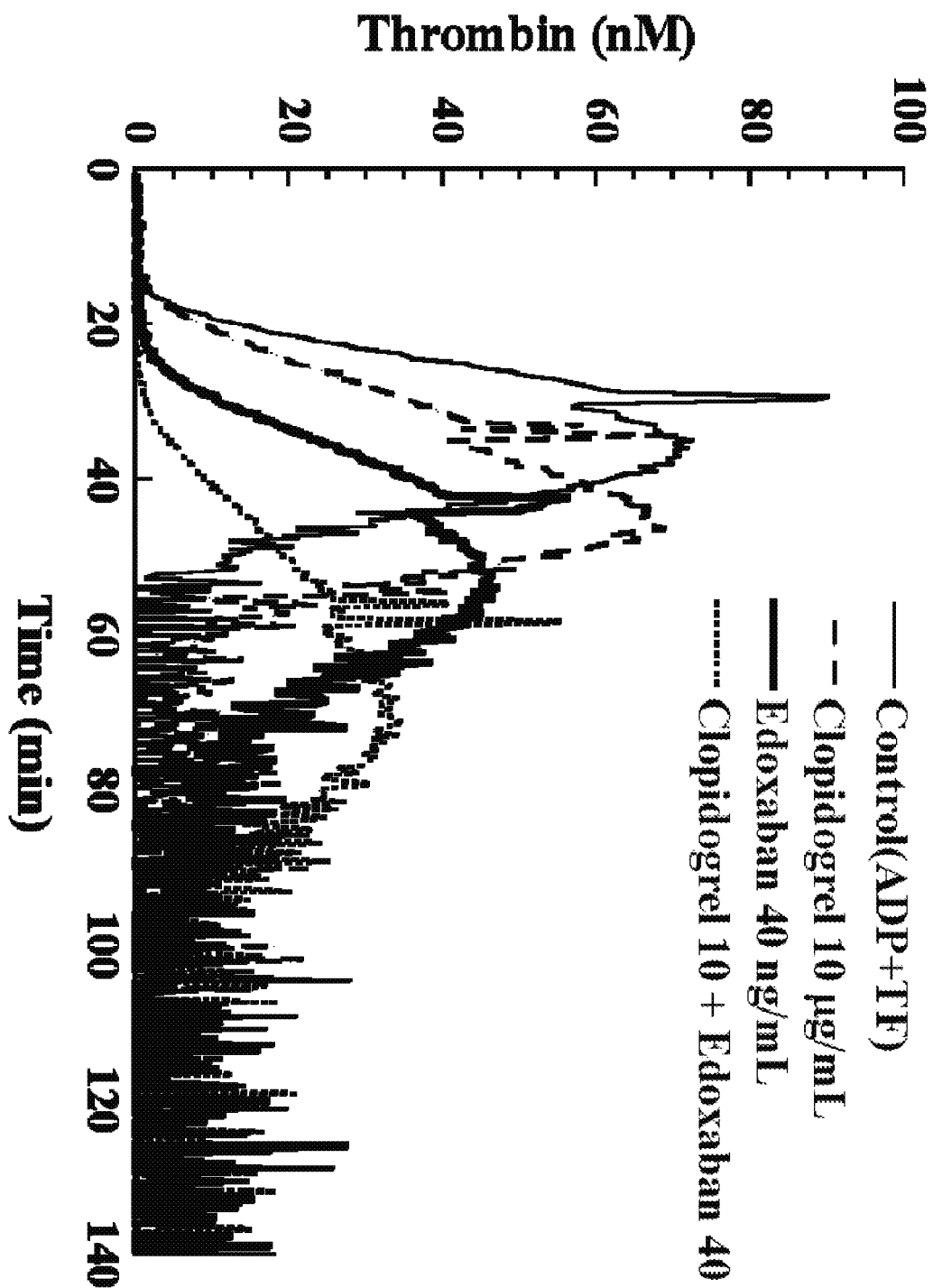
FIG. 3A shows the effects of control, Clopidogrel (10 μg/mL), Edoxaban (40 ng/mL), and Clopidogrel (10 μg/mL)+Edoxaban (40 ng/mL) on thrombin generation. The longitudinal axis indicates a thrombin concentration (nM), and the horizontal axis indicates a time (min).
Figure 3B:
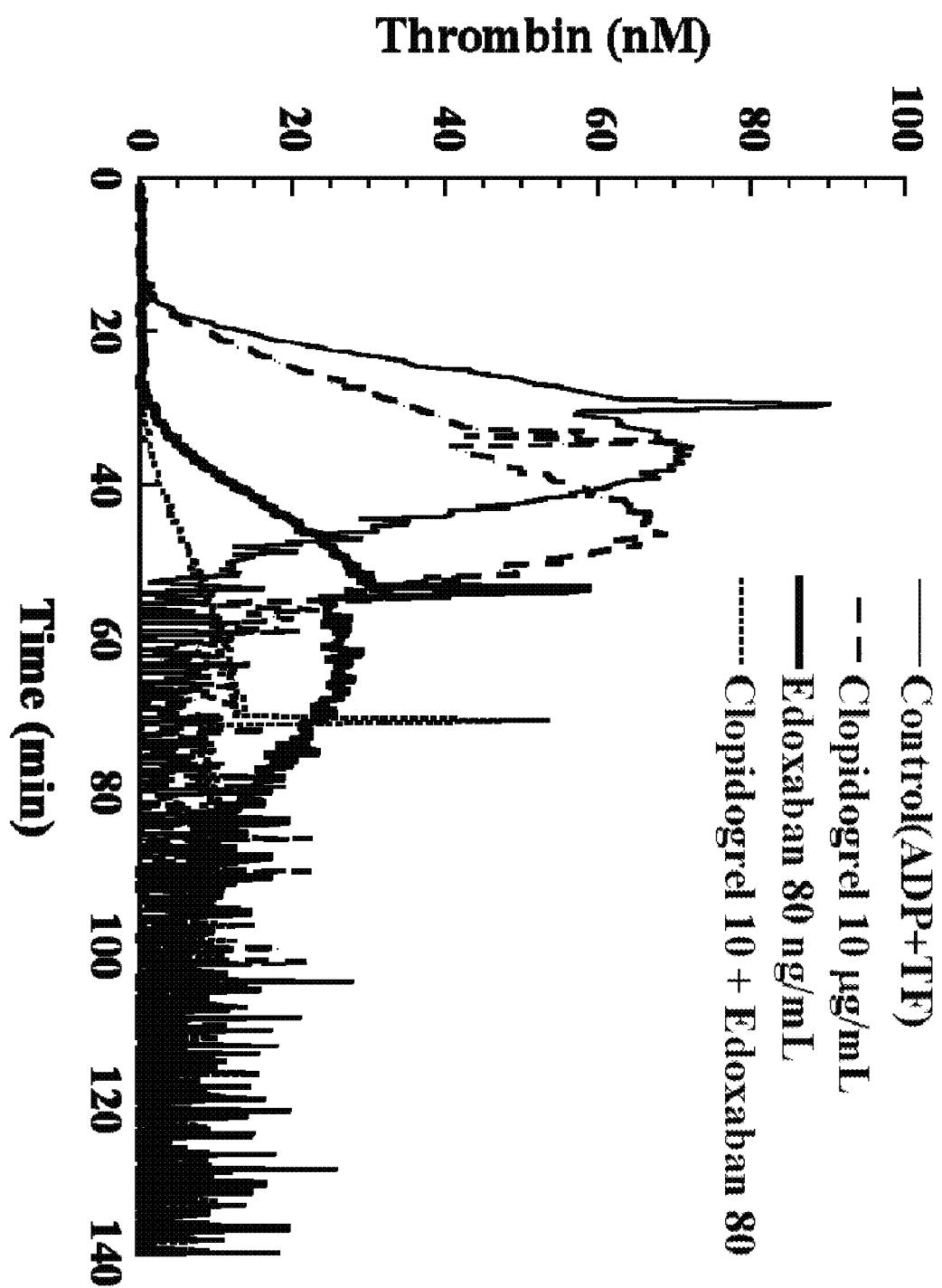
FIG. 3B shows the effects of control, Clopidogrel (10 μg/mL), Edoxaban (80 ng/mL), and Clopidogrel (10 μg/mL)+Edoxaban (80 ng/mL) on thrombin generation. The longitudinal axis indicates a thrombin concentration (nM), and horizontal axis indicates a time (min).
Figure 3C:
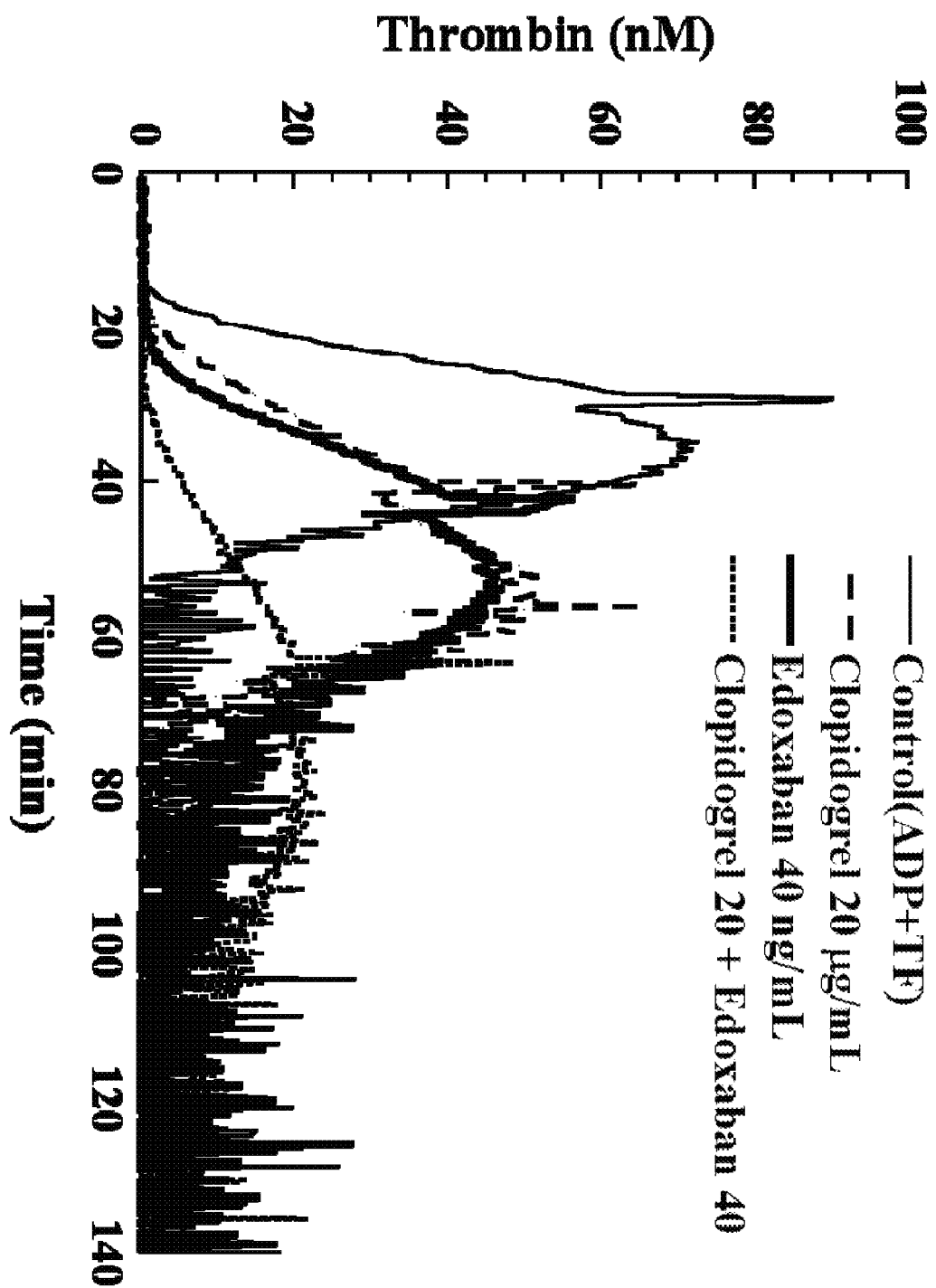
FIG. 3C shows the effects of control, Clopidogrel (20 μg/mL), Edoxaban (40 ng/mL), and Clopidogrel (20 μg/mL)+Edoxaban (40 ng/mL) on thrombin generation. The longitudinal axis indicates a thrombin concentration (nM), and the horizontal axis indicates a time (min).
Figure 3D:
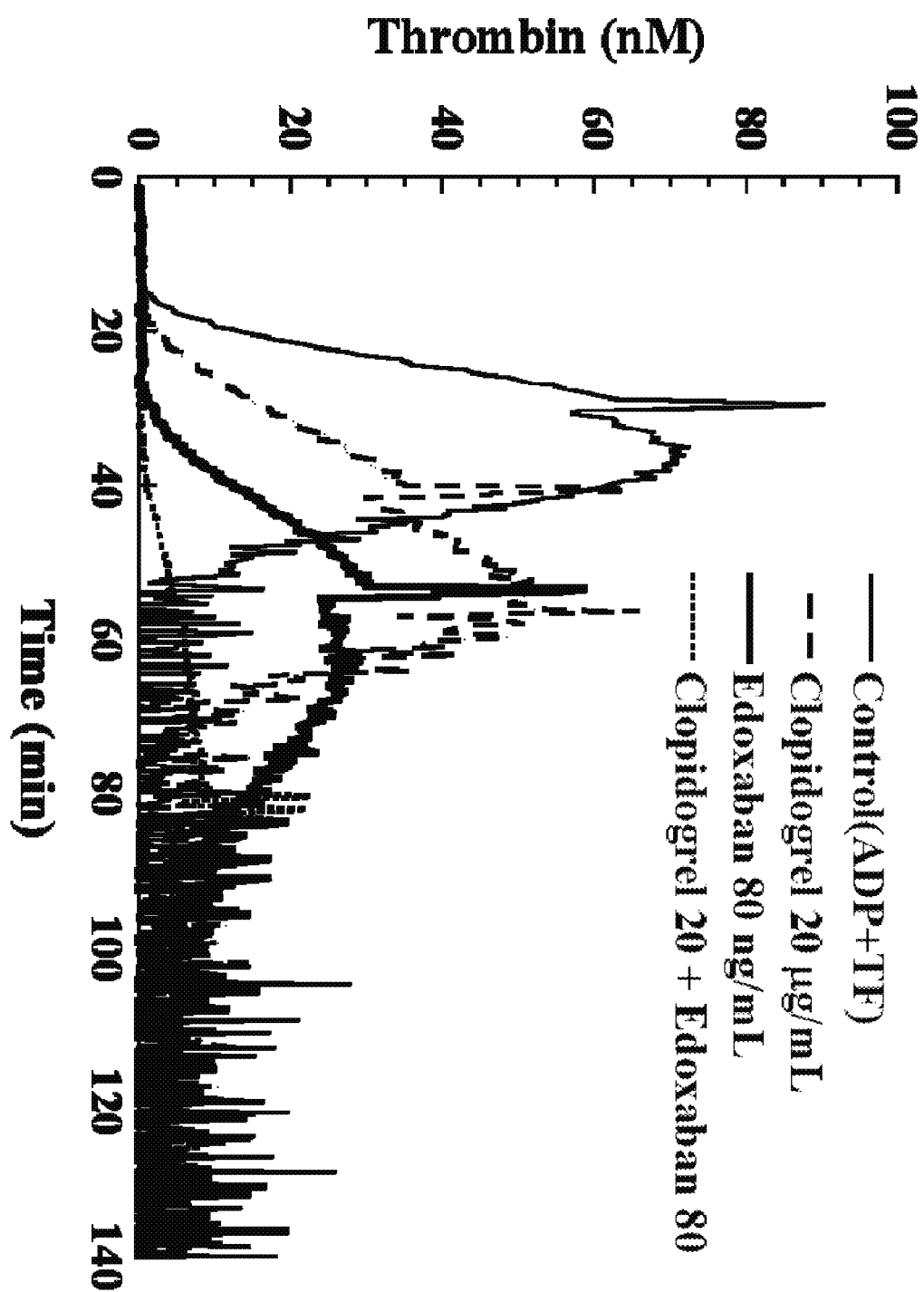
FIG. 3D shows the effects of control, Clopidogrel (20 μg/mL), Edoxaban (80 ng/mL), and Clopidogrel (20 μg/mL)+Edoxaban (80 ng/mL) on thrombin generation. The longitudinal axis indicates a thrombin concentration (nM), and the horizontal axis indicates a time (min).
Figure 4A:
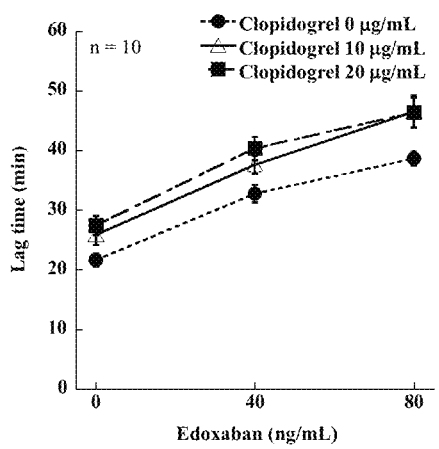
FIG. 4 shows the effects of Edoxaban and/or Clopidogrel on parameters of thrombin generation. A indicates Lag time, B indicates ETP, C indicates Peak, D indicates Time to Peak, and E indicates MaxR.
Figure 4B:
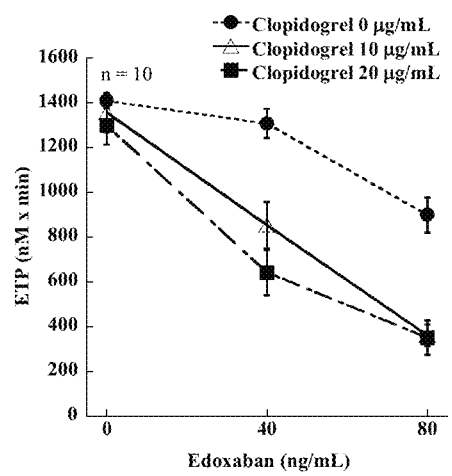
Figure 4C:
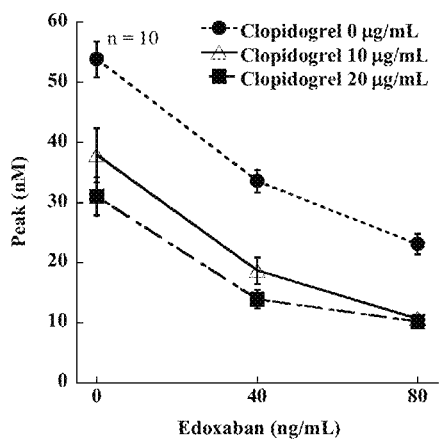
Figure 4D:
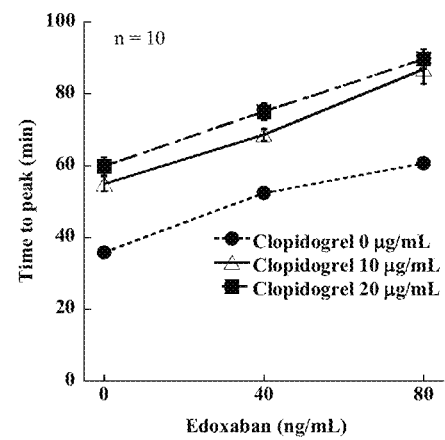
Figure 4E:
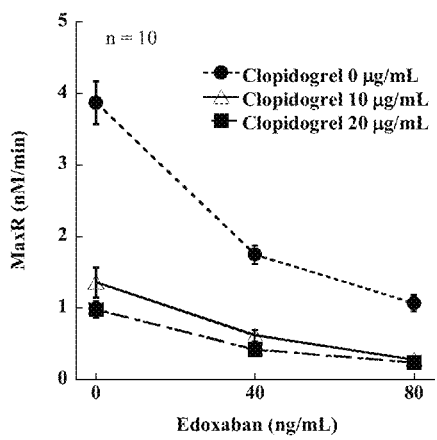

As shown in FIG. 2, when ADP alone was used, stable results could not be obtained in the triplicate measurements. On the other hand, when ADP and TF were used, more stable results than those in the single use of ADP were obtained in the triplicate measurements. As the concentration of TF was increased, much more stable results were obtained.

Individual parameters of thrombin generation, which had been obtained when the ADP concentration had been 10 μM and the TF concentration had been 0.25 pM, were used as controls in the following examples.

Example 1

Confirmation of Combined Effects of Antithrombotic Agents 1

An Edoxaban solution and/or a Clopidogrel solution (5 μL each) were added to a 96-well plate, so that the concentrations of Edoxaban and Clopidogrel in PRP could be the values shown in Table 1, and also, 70 μL of human PRP was added to the plate. Moreover, 20 μL of a solution prepared by mixing a 120 μM ADP solution (final concentration: 10 μM) and a 3 pM TF solution (final concentration: 0.25 pM) in equal volumes was added to the plate, and the obtained mixture was then incubated at 37° C.

Subsequently, individual parameters were calculated in the same manner as that in the above "Studies regarding measurement conditions."

TABLE 1

| | (1) | (2) | (3) | (4) | (5) | (6) | (7) | (8) |
|---|---|---|---|---|---|---|---|---|
| Edoxaban tosilate hydrate (ng/mL) | 40 | 80 | — | — | 40 | 40 | 80 | 80 |
| Active metabolite of Clopidogrel (μg/mL) | — | — | 10 | 20 | 10 | 20 | 10 | 20 |

The time course of the thrombin concentration is shown in FIGS. 3A to 3D. It was found that each of Edoxaban and the active metabolite of Clopidogrel suppresses the generation of thrombin when the agents are used alone compared to the controls. It was also found that the suppressive effects can be further enhanced by using these agents in combination.

The values of individual parameters are shown in FIG. 4. Using a paired t-test, a two-way analysis of variance, or a Spearman's rank correlation coefficient hypothesis test, comparisons were made on the obtained parameters. Upon performing statistical analyses, all analyses were carried out by two-sided tests, and the significance level was set at less than 5%. The results of the statistical analyses are shown in Table 2. In the table, E40 indicates 40 ng/mL Edoxaban, E80 indicates 80 ng/mL Edoxaban, C10 indicates an active metabolite of Clopidogrel (10 μg/mL), C20 indicates an active metabolite of Clopidogrel (20 μg/mL), and Cx/Ey indicates a combined use of an active metabolite of Clopidogrel (x µg/mL) and Edoxaban (y ng/mL), respectively.

TABLE 2

| No. | Comparison group | Method of analysis | Lag time | ETP | Peak | Time to Peak | MaxR |
|---|---|---|---|---|---|---|---|
| 1 | C10/E40 vs C10 | Paired t-test | <0.0001 | <0.0001 | <0.0001 | <0.0001 | <0.05 |
|   | C10/E40 vs E40 |  | <0.05 | <0.05 | <0.0001 | <0.0001 | <0.0001 |
| 2 | C20/E40 vs C20 | Paired t-test | <0.0001 | <0.0001 | <0.0001 | <0.05 | <0.0001 |
|   | C20/E40 vs E40 |  | <0.05 | <0.0001 | <0.0001 | <0.0001 | <0.0001 |
| 3 | C10/E80 vs C10 | Paired t-test | <0.0001 | <0.0001 | <0.0001 | <0.0001 | <0.05 |
|   | C10/E80 vs E80 |  | <0.05 | <0.0001 | <0.0001 | <0.0001 | <0.0001 |
| 4 | C20/E80 vs C20 | Paired t-test | <0.0001 | <0.0001 | <0.0001 | <0.0001 | <0.0001 |
|   | C20/E80 vs E80 |  | <0.05 | <0.05 | <0.0001 | <0.0001 | <0.0001 |
| 5 | Control vs C10 | Paired t-test | <0.05 | 1.119 | <0.05 | <0.0001 | <0.0001 |
|   | Control vs C20 |  | <0.05 | 0.424 | <0.001 | <0.0001 | <0.0001 |
| 6 | All groups | Two-way analysis of variance | 0.2829 | <0.0001 | 0.0583 | <0.05 | <0.0001 |
| 7 | C10 vs C10/E40 | Paired t-test | <0.0001 | <0.0001 | <0.0001 | <0.0001 | <0.05 |
|   | C10 vs C10/E80 |  | <0.0001 | <0.0001 | <0.0001 | <0.0001 | <0.05 |
| 8 | C20 vs C20/E40 | Paired t-test | <0.0001 | <0.0001 | <0.0001 | <0.05 | <0.0001 |
|   | C20 vs C20/E80 |  | <0.0001 | <0.0001 | <0.0001 | <0.0001 | <0.0001 |
| 9 | C10, C10/E40, C10/E80 | Spearman's rank correlation coefficient hypothesis test | <0.0001 | <0.0001 | <0.0001 | <0.0001 | <0.0001 |
| 10 | C20, C20/E40, C20/E80 | Spearman's rank correlation coefficient hypothesis test | <0.0001 | <0.0001 | <0.0001 | <0.0001 | <0.0001 |
| 11 | Control vs E40 | Paired t-test | <0.0001 | 0.2378 | <0.0001 | <0.0001 | <0.0001 |
|    | Control vs E80 |  | <0.0001 | <0.0001 | <0.0001 | <0.0001 | <0.0001 |
| 12 | Control, E40, E80 | Spearman's rank correlation coefficient hypothesis test | <0.0001 | <0.0001 | <0.0001 | <0.0001 | <0.0001 |

It was found that Edoxaban exhibits a concentration-dependent and significant effect on Lag time, Peak, Time to Peak, and MaxR, in the direction of suppressing thrombin generation (Nos. 11 and 12). It was found that the active metabolite of Clopidogrel significantly suppresses thrombin generation, in terms of Lag time, Peak, Time to Peak, and MaxR (No. 5). When a combined use group of Edoxaban and the active metabolite of Clopidogrel was compared with a single use group of Edoxaban or the active metabolite of Clopidogrel, a significant difference was found in all of the parameters (Nos. 1 to 4). It was also found that the combined effects depend on the concentration of Edoxaban (Nos. 9 and 10). Moreover, as a result of the two-way analysis of variance (No. 6), a significant difference was found in ETP and Time to Peak, and thus, it was also found that a more potent suppressive effect on thrombin generation is obtained when Edoxaban is used in combination with the metabolite of Clopidogrel.

Example 2

Confirmation of Combined Effects of Antithrombotic Agents 2

1/200 volume of a Ticagrelor solution was added to human PRP, and the obtained mixture was then incubated at room temperature for 15 minutes. 75 µL of Ticagrelor-containing PRP was added to a 96-well plate, and 5 µL of Edoxaban solution was then added thereto. Moreover, 20 µL of a solution prepared by mixing 120 µM ADP (final concentration: 10 µM) and 3 pM TF (final concentration: 0.25 pM) in equal volumes was added to the plate, and the obtained mixture was then incubated at 37° C.

An Edoxaban solution was added to the 96-well plate, so that the concentrations of the compounds could be the value shown in Table 3, and thereafter, 70 µL of human PRP was added thereto. Moreover, 20 µL of a solution prepared by mixing a 120 µM ADP solution (final concentration: 10 µM) and a 3 pM TF solution (final concentration: 0.25 pM) in equal volumes was added to the plate, and the obtained mixture was then incubated at 37° C.

Subsequently, individual parameters were calculated in the same manner as that in the above "Studies regarding measurement conditions."

TABLE 3

|  | (1) | (2) | (3) | (4) | (5) |
|---|---|---|---|---|---|
| Edoxaban tosilate hydrate (ng/mL) | 40 | 80 | — | 40 | 80 |
| Ticagrelor (µg/mL) | — | — | 3 | 3 | 3 |

Figure 5B:
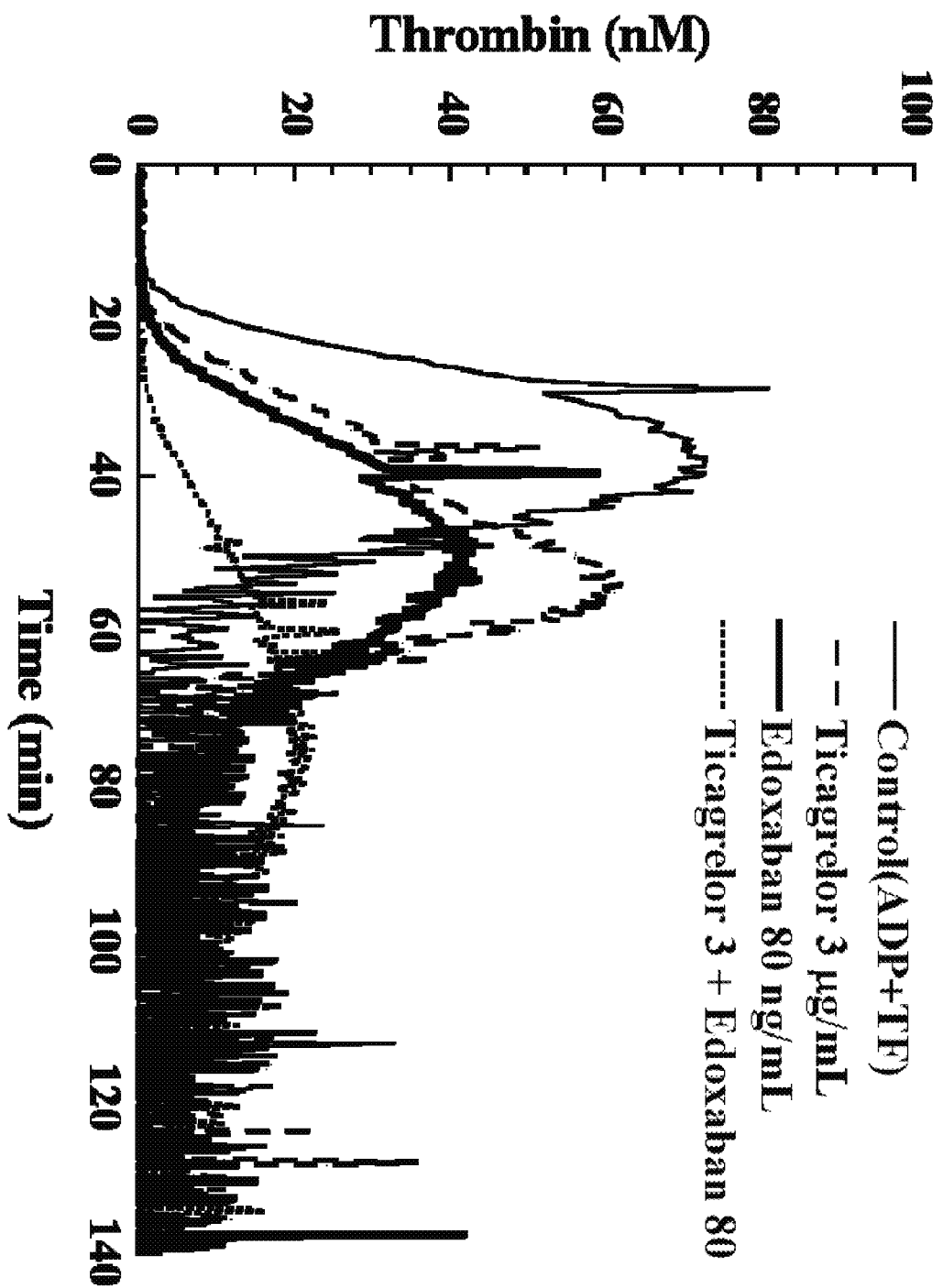
FIG. 5B shows the effects of control, Ticagrelor (3 μg/mL), Edoxaban (80 ng/mL), and Ticagrelor (3 μg/mL)+Edoxaban (80 ng/mL) on thrombin generation. The longitudinal axis indicates a thrombin concentration (nM), and the horizontal axis indicates a time (min).
Figure 6A:
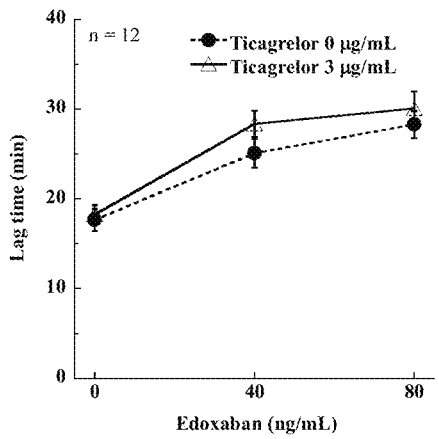
FIG. 6 shows the effects of Edoxaban and/or Ticagrelor on thrombin generation. A indicates Lag time, B indicates ETP, C indicates Peak, D indicates Time to Peak, and E indicates MaxR.
Figure 6B:
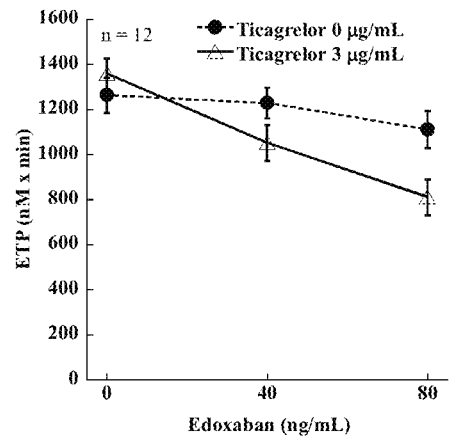
Figure 6C:
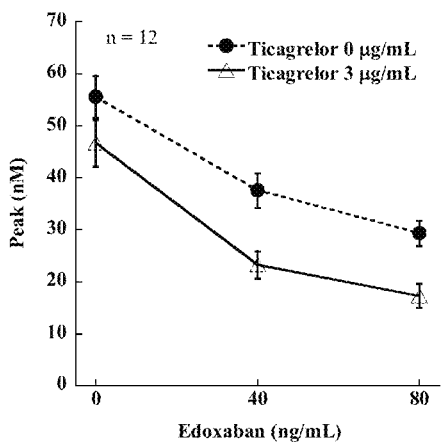
Figure 6D:
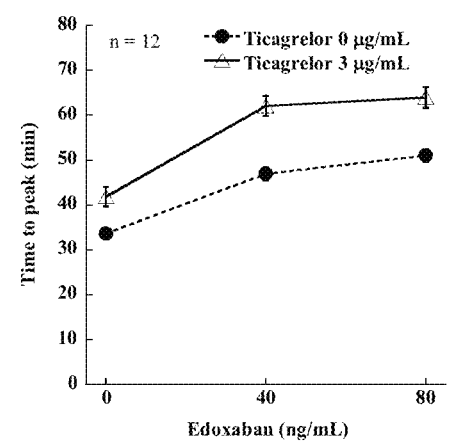
Figure 6E:
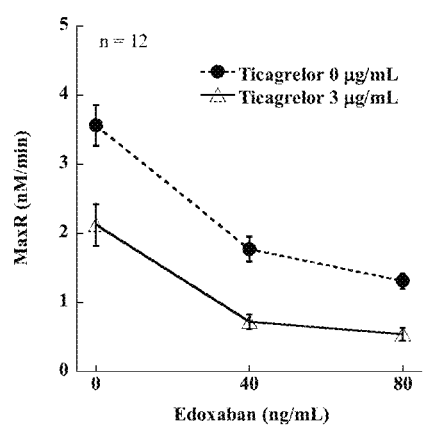

The time course of the thrombin concentration is shown in FIGS. 5A and 5B. It was found that each of Edoxaban and Ticagrelor suppresses the generation of thrombin when the agents are used alone compared to the controls. It was also found that the suppressive effects can be further enhanced by using these agents in combination.

The values of individual parameters are shown in FIG. 6. Using a paired t-test, a two-way analysis of variance, or a Spearman's rank correlation coefficient hypothesis test, comparisons were made on the obtained parameters. Upon performing statistical analyses, all analyses were carried out by two-sided tests, and the significance level was set at less than 5%. The results of the statistical analyses are shown in Table 4. In the table, E40 indicates 40 ng/mL Edoxaban, E80 indicates 80 ng/mL Edoxaban, T3 indicates 3 µg/mL Ticagrelor, and T3/Ey indicates a combined use of Ticagrelor (3 µg/mL) and Edoxaban (y ng/mL), respectively.

TABLE 4

| No. | Comparison group | Method of analysis | Lag time | ETP | Peak | Time to Peak | MaxR |
|---|---|---|---|---|---|---|---|
| 1 | T3/E40 vs T3 | Paired t-test | <0.0001 | <0.05 | <0.0001 | <0.0001 | <0.05 |
|   | T3/E40 vs E40 |  | 0.0650 | <0.05 | <0.05 | <0.0001 | <0.0001 |
| 2 | T3/E80 vs T3 | Paired t-test | <0.0001 | <0.0001 | <0.0001 | <0.0001 | <0.0001 |
|   | T3/E80 V3 E80 |  | 0.5308 | <0.05 | <0.0001 | <0.0001 | <0.0001 |
| 3 | Control vs T3 | Paired t-test | 0.5721 | <0.05 | <0.05 | <0.05 | <0.05 |
| 4 | All groups | Two-way analysis of variance | 0.6703 | <0.05 | 0.7145 | 0.1643 | 0.2561 |
| 5 | T3 vs T3/E40 | Paired t-test | <0.0001 | <0.05 | <0.0001 | <0.0001 | <0.05 |
|   | T3 vs T3/E80 |  | <0.0001 | <0.0001 | <0.0001 | <0.0001 | <0.0001 |
| 6 | T3, T3/E40, T3/E80 | Spearman's rank correlation coefficient hypothesis test | <0.0001 | <0.0001 | <0.0001 | <0.0001 | <0.0001 |
| 7 | Control vs E40 |  | <0.0001 | 0.6824 | <0.0001 | <0.0001 | <0.0001 |
|   | Control vs E80 | Paired t-test | <0.0001 | <0.05 | <0.0001 | <0.0001 | <0.0001 |
| 8 | Control, E40, E80 | Spearman's rank correlation coefficient hypothesis test | <0.0001 | 0.1044 | <0.0001 | <0.0001 | <0.0001 |

Edoxaban concentration-dependently and significantly suppressed thrombin generation, in terms of Lag time, Peak, Time to Peak, and MaxR (Nos. 7 and 8). It was found that Ticagrelor significantly suppresses thrombin generation, in terms of Peak, Time to Peak, and MaxR (No. 3). When a combined use group of Edoxaban and Ticagrelor was compared with a single use group of Edoxaban or Ticagrelor, a significant difference was found in ETP, Peak, Time to Peak, and MaxR (Nos. 1 and 2). It was found that the combined effects depend on the concentration of Edoxaban (No. 6). Moreover, as a result of the two-way analysis of variance (No. 4), a significant difference was found in ETP, and thus, it was also found that a more potent suppressive effect on thrombin generation is obtained when Edoxaban is used in combination with Ticagrelor.

From the aforementioned results, it was found that, if the in vitro assay system of the present invention is used, the combined effects of antithrombotic agents can be evaluated from various viewpoints, without using an in vivo assay system.

INDUSTRIAL APPLICABILITY

The present invention can be used to determine the combined effects, when antithrombotic agents are used in combination.

The invention claimed is:

1. A method for measuring thrombin generation comprising:
   (a) adding an anticoagulant, a $P2Y_{12}$ receptor inhibitor, adenosine diphosphate and tissue factor to platelet rich plasma;
   (b) adding to the platelet rich plasma a fluorogenic thrombin substrate comprising a fluorogenic probe and a calcium-containing solution, wherein said substrate is degraded by thrombin to provide the fluorogenic probe;
   (c) exciting the probe with light and measuring the fluorescence intensity of the probe, and
   (d) converting the fluorescence intensity to a thrombin concentration,
   wherein the adenosine diphosphate and the tissue factor are effective in combination to provoke stable thrombin generation in the absence of the anticoagulant and $P2Y_{12}$ receptor inhibitor.

2. The method according to claim 1, wherein the anticoagulant is a factor Xa inhibitor.

3. The method according to claim 2, wherein the factor Xa inhibitor is edoxaban.

4. The method according to claim 3, wherein the $P2Y_{12}$ receptor inhibitor is clopidogrel or ticagrelor.

5. The method according to claim 3, wherein the final concentration of the adenosine diphosphate in step (a) is 5 to 20 µM.

6. The method according to claim 3, wherein the final concentration of the tissue factor in step (a) is 0.05 to 0.25 pM.

7. The method according to claim 2, wherein the $P2Y_{12}$ receptor inhibitor is clopidogrel or ticagrelor.

8. The method according to claim 2, wherein the final concentration of the adenosine diphosphate in step (a) is 5 to 20 µM.

9. The method according to claim 2, wherein the final concentration of the tissue factor in step (a) is 0.05 to 0.25 pM.

10. The method according to claim 1, wherein the $P2Y_{12}$ receptor inhibitor is clopidogrel or ticagrelor.

11. The method according to claim 10, wherein the final concentration of the adenosine diphosphate in step (a) is 5 to 20 µM.

12. The method according to claim 10, wherein the final concentration of the tissue factor in step (a) is 0.05 to 0.25 pM.

13. The method according to claim 1, wherein the final concentration of the adenosine diphosphate in step (a) is 5 to 20 µM.

14. The method according to claim 13, wherein the final concentration of the tissue factor in step (a) is 0.05 to 0.25 pM.

15. The method according to claim 1, wherein the final concentration of the tissue factor in step (a) is 0.05 to 0.25 pM.

16. The method according to claim 1, wherein
   the anticoagulant is edoxaban,
   the $P2Y_{12}$ receptor inhibitor is clopidogrel or ticagrelor,
   the final concentration of the adenosine diphosphate in step (a) is 5 to 20 µM, and
   the final concentration of the tissue factor in step (a) is 0.05 to 0.25 pM.

17. The method according to claim 1, wherein the fluorogenic thrombin substrate is Z-Gly-Gly-Arg-AMC HCl.

18. The method according to claim 1, wherein the fluorescence intensity is measured with a fluorophotometer.

19. The method according to claim 1, wherein the concentration of the generated thrombin is indirectly determined by the measurement of fluorescence intensity.

20. The method according to claim 1, wherein a thrombin calibration curve is used to convert the fluorescence intensity to the thrombin concentration.

21. A method for measuring thrombin generation comprising:

(a) obtaining platelet rich plasma from blood collected from a mammal to which an anticoagulant and a $P2Y_{12}$ receptor inhibitor have been administered;
(b) adding adenosine diphosphate and tissue factor to the obtained platelet rich plasma;
(c) further adding to the platelet rich plasma a calcium-containing solution and a fluorogenic thrombin substrate comprising a fluorogenic probe, which is degraded by thrombin to provide the fluorogenic probe;
(d) exciting the probe with light and measuring the fluorescence intensity, and
(e) converting the fluorescence intensity to a thrombin concentration, wherein the adenosine diphosphate and the tissue factor are effective in combination to provoke stable thrombin generation in the absence of the anticoagulant and $P2Y_{12}$ receptor inhibitor.

22. A method for evaluating the combined effects of an anticoagulant and a $P2Y_{12}$ receptor inhibitor, comprising:
(a) obtaining platelet rich plasma from blood collected from a mammal to which an anticoagulant and a $P2Y_{12}$ receptor inhibitor have been administered;
(b) adding adenosine diphosphate and tissue factor to the obtained platelet rich plasma;
(c) further adding to the platelet rich plasma a calcium-containing solution and a fluorogenic thrombin substrate comprising a fluorogenic probe, which is degraded by thrombin to provide the fluorogenic probe;
(d) exciting the probe with light and measuring the fluorescence intensity and converting the fluorescence intensity to a thrombin concentration;
(e) obtaining platelet rich plasma from blood collected from a mammal to which an anticoagulant or a $P2Y_{12}$ receptor inhibitor have been administered, or to which none of the agents have been administered;
(f) adding adenosine diphosphate and tissue factor to the obtained platelet rich plasma;
(g) further adding to the platelet rich plasma a calcium-containing solution and a fluorogenic thrombin substrate comprising a fluorogenic probe, which is degraded by thrombin to provide the fluorogenic probe;
(h) exciting the probe with light and measuring the fluorescence intensity and converting the fluorescence intensity to a thrombin concentration; and
(i) comparing the value obtained in step (d) with the value obtained in step (h), wherein the adenosine diphosphate and the tissue factor are effective in combination to provoke stable thrombin generation in the absence of the anticoagulant and $P2Y_{12}$ receptor inhibitor.

23. A method for measuring thrombin generation comprising:
(a) adding adenosine diphosphate and tissue factor to platelet rich plasma that contains an anticoagulant and a $P2Y_{12}$ receptor inhibitor;
(b) adding to the platelet rich plasma a fluorogenic thrombin substrate comprising a fluorogenic probe and a calcium-containing solution, wherein said substrate is degraded by thrombin to provide the fluorogenic probe;
(c) exciting the probe with light and measuring the fluorescence intensity, and
(d) converting the fluorescence intensity to a thrombin concentration, wherein the adenosine diphosphate and the tissue factor are effective in combination to provoke stable thrombin generation in the absence of the anticoagulant and $P2Y_{12}$ receptor inhibitor.

* * * * *